US00PP10086P

United States Patent [19]

Rother

[11] Patent Number: Plant 10,086

[45] Date of Patent: Oct. 28, 1997

[54] PETUNIA PLANT NAMED 'PURPLE SUNSPOT'

[76] Inventor: Reinhard W. Rother, 56 Emerald Monbulk Road, Emerald, Victoria 3782, Australia

[21] Appl. No.: 680,363

[22] Filed: Jul. 15, 1996

[51] Int. Cl.[6] ..... A01H 5/00

[52] U.S. Cl. ..... Plt./68.1

[58] Field of Search ..... Plt./68.1

*Primary Examiner*—James R. Feyrer
*Attorney, Agent, or Firm*—C. A. Whealy

[57] ABSTRACT

A distinct cultivar of Petunia plant named 'Purple Sunspot', characterized by its dark purple flowers that face upwards; moderate to vigorous growth habit and rapid growth rate; spreading and decumbent plant habit; freely branching habit; early flowering; very floriferous with numerous flowers per plant; and tolerance to rain, drought and temperature extremes.

2 Drawing Sheets

The present invention relates to a new and distinct cultivar of Petunia plant, botanically known as *Petunia axillaris*, and hereinafter referred to by the cultivar name Purple Sunspot.

The new cultivar is a product of a planned breeding program conducted by the inventor in Emerald, Victoria, Australia. The objective of the breeding program was to create new Petunia cultivars having large flowers, a spreading plant habit, and desirable flower colors.

The new cultivar originated from a cross made by the inventor of the inventor's proprietary Petunia selection No. 492-X as the male or pollen parent with the inventor's proprietary Petunia selection No. 592-Y as the female or seed parent.

The cultivar Purple Sunspot was discovered and selected by the inventor as a flowering plant within the progeny of the stated cross in a controlled environment in Emerald, Victoria, Australia. Asexual reproduction of the new cultivar by terminal cuttings taken at Emerald, Victoria, Australia, has shown that the unique features of this new Petunia are stable and reproduced true to type in successive generations.

The cultivar Purple Sunspot has not been observed under all possible environmental conditions. The phenotype may vary somewhat with variations in environment such as temperature and light intensity, without, however, any variance in genotype. The following observations, measurements and comparisons describe plants grown in Emerald, Victoria, Australia, under commercial production conditions.

The following traits have been repeatedly observed and are determined to be the unique characteristics of 'Purple Sunspot'. These characteristics in combination distinguish 'Purple Sunspot' as a new and distinct cultivar:

1. Dark purple flowers that face upwards.
2. Moderate to vigorous growth habit and rapid growth rate.
3. Spreading and decumbent plant habit.
4. Freely branching habit. Plants do not require pinching.
5. Early flowering.
6. Very floriferous with numerous flowers per plant.
7. Tolerant to rain, drought and temperature extremes.

The cultivar Purple Sunspot is most similar in flower color to the cultivar Pampas Fire (disclosed in U.S. Plant Pat. No. 9,408). The cultivar differs from the cultivar Pampas Fire in the following characteristics:

1. Plants of the cultivar Purple Sunspot are more compact than plants of the cultivar Pampas Fire.
2. Plants of the cultivar Purple Sunspot have longer internodes than plants of the cultivar Pampas Fire.
3. Stems of the cultivar Purple Sunspot contain anthocyanin whereas stems of the cultivar Pampas Fire do not show any red coloration.

4. Leaves of the cultivar Purple Sunspot are smaller than leaves of the cultivar Pampas Fire.
5. Leaves of the cultivar Purple Sunspot are elliptic in shape whereas leaves of the cultivar Pampas Fire are ovate in shape.
6. Flowers are smaller on plants of the cultivar Purple Sunspot than plants of the cultivar Pampas Fire.
7. Plants of the cultivar Purple Sunspot have smaller sepals than plants of the cultivar Pampas Fire.
8. The anther color of plants of the cultivar Purple Sunspot is blue whereas the anther color of plants of the cultivar Pampas Fire is purple.

A detailed comparison of the cultivars Purple Sunspot and Pampas Fire appears in Chart A at the end of the specification.

The accompanying colored photographs illustrate the overall appearance of the new cultivar, showing the colors as true as it is reasonably possible to obtain in colored reproductions of this type.

The first photograph comprises a side perspective view of a typical combination hanging basket plant of the cultivar Purple Sunspot.

The second photograph comprises a close-up view of individual flowers of the cultivar Purple Sunspot. Flower and foliage colors may appear different than the actual colors due to light reflectance.

In the following description, color references are made to The Royal Horticultural Society Colour Chart except where general terms of ordinary dictionary significance are used. Measurements are averages from ten specimens selected at random from five plants.

Botanical classification: *Petunia axillaris* cultivar Purple Sunspot.

Parentage:

*Male or pollen parent.*—*Petunia axillaris*, inventor's proprietary selection No. 492-X.

*Female or seed parent.*—*Petunia axillaris*, inventor's proprietary selection No. 592-Y.

Propagation:

*Type cutting.*—Terminal vegetative cuttings.

*Time to initiate roots.*—About ten days at 21C soil temperature.

*Rooting habit.*—Numerous, fine, fibrous, and well-branched.

Plant description:

*Form.*—Indeterminate, decumbent, diffuse spreading, viscid, glandular pubescent.

*Branching habit.*—Freely branching.

*Plant height.*—About 13.2 cm.

*Plant width.*—About 59.6 cm.

*Vigor.*—Moderate to vigorous.

*Crop time.*—8 to 9 weeks from a unrooted cutting to a 10.5-cm finished and flowering container.

*Foliage description.*—Leaves simple, generally symmetrical, sessile, and long persisting. Leaves at first whorled, later alternate, somewhat fleshy. Size (largest leaves): Length: About 6.1 cm. Width: About 3.4 cm. Thickness: About 1.5 mm. Shape: Elliptic. Aspect: Horizontal to upwards. Apex: Acute to acuminate. Base: Attenuate. Margin: Entire. Texture: Sparsely pubescent. Color: Young foliage upper side: 137A. Young foliage under side: 137C. Mature foliage upper side: 137A. Mature foliage under side: 137C.

*Stem description.*—Stems spreading or hanging a length of one at least meter, hirsute. Stem diameter: About 3.5 mm. Internode length: Long, about 4.3 cm. Stem color: Green, 144A, with red, 64A, areas on upper stem surfaces and at internodes.

Flower description:

*Flower type and habit.*—Large, single, salverform flowers, facing upwards, axillary. Calyx five-parted, petals united into a flower tube.

*Natural flowering season.*—Long day responsive, continuously flowers from spring through fall in Northern Hemisphere.

*Quantity.*—Numerous flowers per plant.

*Corolla.*—Diameter: About 5.4 cm. Height: About 5.1 cm. Flower tube width at distal end: Narrow, about 1.3 cm. Petal quantity: Five, fused. Petal apex: Acuminate. Margin: Entire. Texture: Pubescent on outside, smooth and satiny on inside. Color: Flower throat (inside): 82A/83A. Flower throat vein color (inside): 83B. Flower tube color (outside): 83B. Flower tube vein color (outside): 83A. Petal color, inside: Richer than 74A. Petal vein color, inside: 83B. Petal color, outside: 81A to 81C. Petal vein color, outside: 83A.

*Sepals.*—Quantity: Five. Size: Length: About 2.1 cm. Width: About 3.2 mm. Shape: Elliptic. Apex: Obtuse. Margin: Entire. Texture: Pubescent. Aspect: Upright. Color: Inside: 137A. Outside: 137B.

*Pedicel.*—Aspect: Upright. Size: Length: Short to medium, about 2.1 cm. Width: Narrow, about 1.5 mm. Texture: Pubescent. Color: 144A with hints of 64A.

*Reproductive organs.*—Stigma level with anthers, superior ovary. Stamens: Stamen number: Five, four are didymous. Anther color: Blue. Filament color: Green white, violet towards anther. Pistils: Stigma color: Green. Style color: Yellow green.

Disease resistance: No known Petunia diseases observed to date.

Fruit and seed production: Rarely observed.

*Fruit.*—Capsule with two undivided valves.

*Seeds.*—Minute, spherical.

CHART A

| CHARACTERISTIC | 'PURPLE SUNSPOT' | 'PAMPAS FIRE' |
|---|---|---|
| PLANT WIDTH | 59.6 cm | 75.6 cm |
| INTERNODE LENGTH | 4.3 cm | 3.2 cm |
| RED AREAS ON STEMS AND PEDICELS | Present | Absent |
| LEAF LENGTH | 6.1 cm | 9.6 cm |
| LEAF WIDTH | 3.4 cm | 4.5 cm |
| LEAF SHAPE | Elliptic | Ovate |
| COROLLA DIAMETER | 5.4 cm | 7.6 cm |
| COROLLA HEIGHT | 5.1 cm | 6 cm |
| FLOWER TUBE WIDTH | 1.3 cm | 1.6 cm |
| SEPAL LENGTH | 2.1 cm | 2.7 cm |
| SEPAL WIDTH | 3.2 mm | 7.3 mm |
| PETAL COLOR, OUTSIDE | 81A to 81C | 80C |
| ANTHER COLOR | Blue | Violet |

It is claimed:

1. A new and distinct cultivar of Petunia plant named 'Purple Sunspot', as illustrated and described.

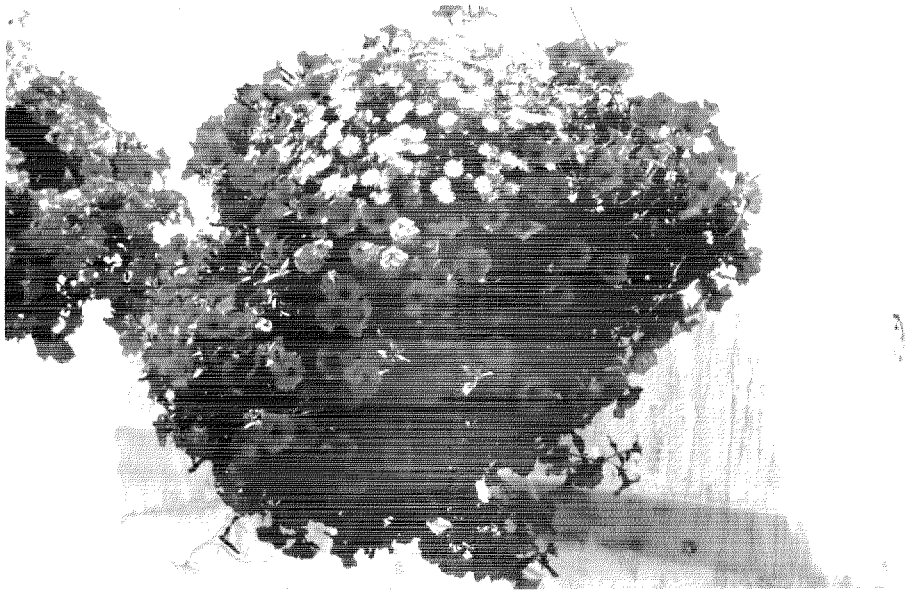

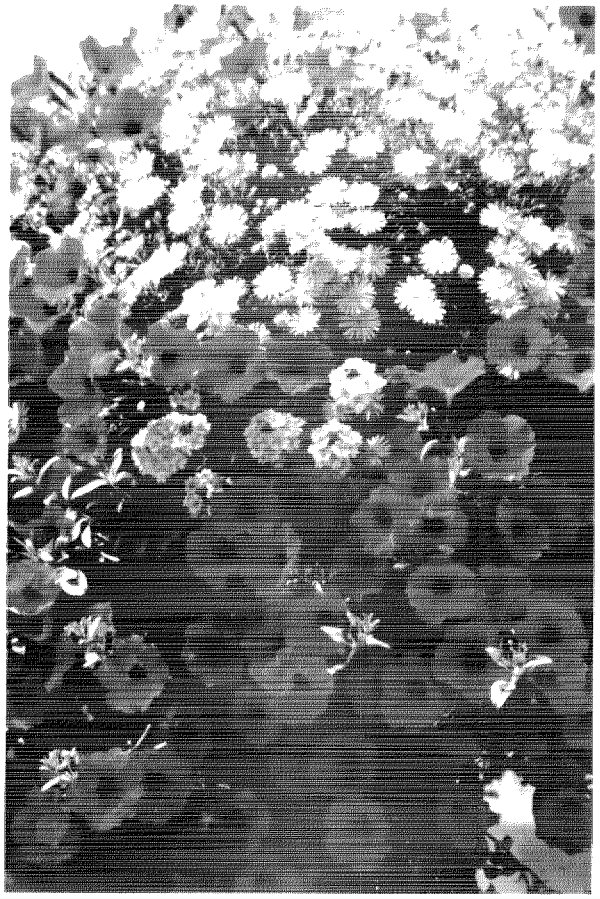

* * * * *